United States Patent [19]

Kajiyama et al.

[11] Patent Number: 4,573,792
[45] Date of Patent: Mar. 4, 1986

[54] METHOD OF AND APPARATUS FOR QUANTITATIVE ANALYSIS IN ACCORDANCE WITH CARS

[75] Inventors: Koichi Kajiyama, Hiratsuka; Norio Moro, Yamato; Kazuaki Sajiki, Fujisawa; Tadayoshi Yamaguchi, Hiratsuka, all of Japan

[73] Assignee: Kabushiki Kaisha Komatsu Seisakusho, Tokyo, Japan

[21] Appl. No.: 480,482

[22] Filed: Mar. 30, 1983

[30] Foreign Application Priority Data

Mar. 31, 1982 [JP] Japan .................................. 57-54627
Jul. 9, 1982 [JP] Japan .................................. 57-119636

[51] Int. Cl.$^4$ ........................ G01J 3/44; G01N 21/65
[52] U.S. Cl. ................................................. 356/301
[58] Field of Search ........................................ 356/301

[56] References Cited

FOREIGN PATENT DOCUMENTS

| | | |
|---|---|---|
| 1547217 | 11/1969 | Fed. Rep. of Germany . |
| 2308034 | 8/1973 | Fed. Rep. of Germany . |
| 2320166 | 10/1973 | Fed. Rep. of Germany . |
| 2216877 | 10/1973 | Fed. Rep. of Germany . |
| 2616377 | 11/1976 | Fed. Rep. of Germany . |
| 105059 | 4/1974 | German Democratic Rep. . |

OTHER PUBLICATIONS

Nibler et al., *Optics Communications*, vol. 18, No. 3, Aug. 1976, pp. 371-373.
Tolles et al., *Applied Spectroscopy*, vol. 31, No. 4, Jul.-Aug. 1977, pp. 253-270.
Bridoux et al., *Journal of Raman Spectroscopy*, vol. 11, No. 6, Dec. 1981, pp. 515-516.
Eckbreth et al., *Prog. Energy Combust. Sci.*, vol. 5, pp. 253-322, (1979).
CARS Concentration Sensitivity With and Without Nonresonant Background Suppression by Eckbreth et al., Final Tech. Report R80-95462811, United Technologies Research Center, (1980).
"CARS Measurements in an Internal Combustion Engine," Applied Optics, vol. 18, No. 22, Nov. 15, 1979.
"Coherent Anti-Stokes Raman Spectroscopy (CARS): Improved Experimental Design and Observation of New Higher-Order Processes," Applied Physics Letters, vol. 28, No. 1, Jan. 1, 1976.

*Primary Examiner*—F. L. Evans
*Attorney, Agent, or Firm*—Michael N. Meller

[57] ABSTRACT

A method of and an apparatus for quantitative analysis in accordance with CARS wherein a first system filled with a material to be measured and a second system filled with a reference material of known concentration are disposed in series; first laser light of a first frequency for excitation is applied to these systems together with second laser light having frequency of wide band width; light passed through these two systems, respectively, is applied to a spectrograph provided with, a multi-channel detector; and quantitative analysis for the material to be measured is effected on the basis of a ratio of intensity between the signal outputs generated in respective different channels of the multi-channel detector and corresponding to the material to be measured and to the reference material respectively. Furthermore, anti-Stokes' light emitted between rotational levels of hydrogen is utilized in the case of quantitative analysis of hydrogen.

5 Claims, 6 Drawing Figures

METHOD OF AND APPARATUS FOR QUANTITATIVE ANALYSIS IN ACCORDANCE WITH CARS

BACKGROUND OF THE INVENTION

1. Field of the Invention

The present invention relates to a method of and apparatus for quantitative analysis in accordance with CARS (Coherent Anti-Stokes Raman Spectroscopy).

2. Description of the Prior Art

CARS is a kind of non-linear Raman spectroscopy which has progressed with the development of high-power laser, and dye laser, and which exhibits a detection sensitivity of around $10^5$ times greater than that of conventional Raman spectroscopy so that CARS is expected to be applied in various fields.

The principle of CARS will be simply described hereinbelow. As illustrated in FIG. 1, when laser light for excitation having frequency $\omega_1$ is irradiated on a material (Raman-active material) RM together, with laser light of the same frequency (Stokes' frequency) $\omega_2$ ($=\omega_1-\Omega$, wherein $\Omega$ is the proper frequency of a molecule of the material RM) as that of Stokes' light of the material RM, very intensive, beam-like anti-Stokes' light (frequency $\omega_3 = \omega_1 + \Omega$) of the material RM is resonantly generated. Such a phenomenon may be interpreted as a four-photon process as illustrated in the energy diagram of FIG. 2. Furthermore, an intensity $I_3$ of the anti-Stokes' light at that time is given by the following expression:

$$I_3 \propto I_1^2 \cdot I_2 \cdot N^2 \qquad (1)$$

wherein N is the density of the material RM, $I_1$ is the intensity of the laser light having frequency $\omega_1$ and $I_2$ is the intensity of the laser light having frequency $\omega_2$. Accordingly, when the intensity $I_3$ of the aforesaid anti-Stokes' light is detected, the concentration of the material RM can be detected. CARS is based on the above-described principle whereby the concentration of a material is measured by detecting the intensity $I_3$ of the aforesaid anti-Stokes' light.

Light detected in accordance with CARS varies remarkably, in actuality, dependent upon variation in intensity of the laser light for excitation, conditions of the optical system and the like. Accordingly, an apparatus for quantitative analysis (apparatus for measuring concentration) in accordance with conventional CARS is constructed in such a manner that signal strength from a system to be measured is corrected by utilizing the signal from a reference cell containing a known reference material as the standard, whereby concentration is measured.

FIG. 3 is a schematic view showing an apparatus for quantitative analysis in accordance with conventional CARS wherein a cell A is filled with a material to be measured, while a cell B is filled with a reference material of a prescribed concentration. The laser light for excitation of frequency $\omega_1$ is reflected with a mirror 1 to be introduced to a beam splitter 2', whilst laser light of frequency $\omega_2$ is applied to a dichroic mirror 2. The laser light for excitation of frequency $\omega_1$ and the laser light of $\omega_2$ are synthesized by means of the dichroic mirror 2, then the resulting synthesized light is split by means of a beam splitter 2' into two portions, a portion of which is applied to a spectrograph 7 through a lens 4, the cell A, a lens 5 and a prism 6, whilst the other portion is applied to a spectrograph 11 through a lens 8, the cell B, a lens 9 and a prism 10 after reflection off of mirror 3. The spectrographs 7 and 11 are provided with detectors 7a and 11a, respectively, and these detectors detect the light intensity being applied to the spectrographs 7 and 11 and convert this intensity into electrical signals.

In the conventional system as mentioned above, however, two systems for signal detection consisting of a first signal detection system involving the spectrograph 7 and the detector 7a and a second signal detection system involving the spectrograph 11 and the detector 11a are required. Also, adjustment of the optical axis must also be effected by means of two systems. Therefore, such a conventional system becomes expensive and adjustment requires much labor.

Furthermore, in the above-described measurement, it is also required that the Raman wavenumber (corresponding to the Stokes' frequency) of a reference material be in the vicinity (within a range of 80 cm$^{-1}$) of that of a material to be determined in order to determine the signal strength of the material to be determined at the same time of that of the reference material.

Supposing that, for example, concentration of hydrogen is measured in accordance with CARS, since the hydrogen molecule has a very high vibrational level of 4169 cm$^{-1}$ as compared with those of other materials, there is no suitable reference material satisfying the above-described condition so that such measurement in which any reference material is utilized could not have heretofore been effected. Notwithstanding this fact, if there is no correction on the basis of a reference material, the measured values obtained involve variation in the intensity of laser light for excitation, or in the conditions of the optical system so that such measurement is not reliable.

SUMMARY OF THE INVENTION

It is a first object of the present invention to provide a method of and apparatus for quantitative analysis in accordance with CARS which is simple in construction wherein portions to be adjusted are reduced by half, but by which correct quantitative analysis can be effected.

Furthermore, a second object of the present invention is to provide a method for measuring the concentration of hydrogen in accordance with CARS whereby hydrogen concentration can be measured with high precision.

In order to attain the aforesaid first object of the present invention, laser light having a frequency of wide stroke width (wide band width) is used as the laser light of frequency $\omega_2$ to be applied to a material to be measured together with the excitation laser light of frequency $\omega_1$; a material having a Raman frequency close to that of the material to be measured, so that it can be covered with the laser light of the aforesaid stroke width, is used as a reference material; furthermore, a first cell filled with the material to be measured and a second cell filled with the reference material are disposed in series with respect to the input laser light; the laser light passed through the aforesaid first and second cells is applied to multi-channel detectors in which the laser light is simultaneously detected by means of different channels at every wavelength; and a concentration of the aforesaid material to be measured is detected from a ratio of intensity between a signal output corresponding to the aforesaid material to be detected and generated in the respective different channels of the detectors of multi-channel and a signal output corresponding to the reference material, whereby correct detection of the concentration is effected by means of one detection system.

Furthermore, in order to attain the aforesaid second object of the present invention, there is proposed a method for measuring the concentration of hydrogen in which the rotational level is utilized in place of the vibrational level of hydrogen. Generally, in the case where CARS is utilized for measuring the concentration of a material, anti-Stokes' light emitted between vibrational levels of the material to be measured is employed. However, it is known that anti-Stokes' light is also emitted between rotational levels in accordance with CARS, although such signal strength is weaker than that of the anti-Stokes' light emitted between vibrational levels. Such anti-Stokes' light emitted between rotational levels has relatively low wavenumber as compared with the anti-Stokes' light emitted between vibrational levels. In the circumstances, according to the present invention, anti-Stokes' light emitted between rotational levels is utilized in a method for measuring the hydrogen concentration in accordance with CARS, whereby a reference material satisfying a prescribed condition can be selected so that measurement of the concentration of hydrogen can be effected with high precision.

DESCRIPTION OF THE PREFERRED EMBODIMENTS

An embodiment of the present invention will be described in detail hereinbelow by referring to the accompanying drawings.

Figure 1:
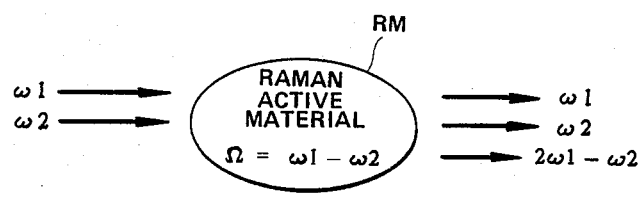
FIG. 1 is a schematic view for explaining the basic principle of CARS utilized in the present invention.
Figure 2:
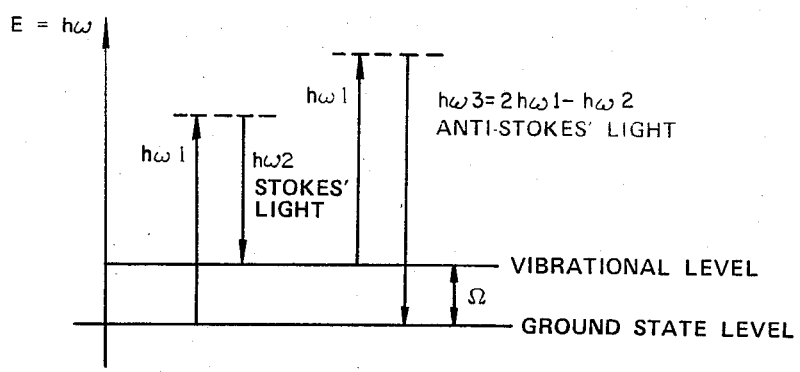
FIG. 2 is an energy diagram for explaining the basic principle of CARS utilized in the present invention.
Figure 3:
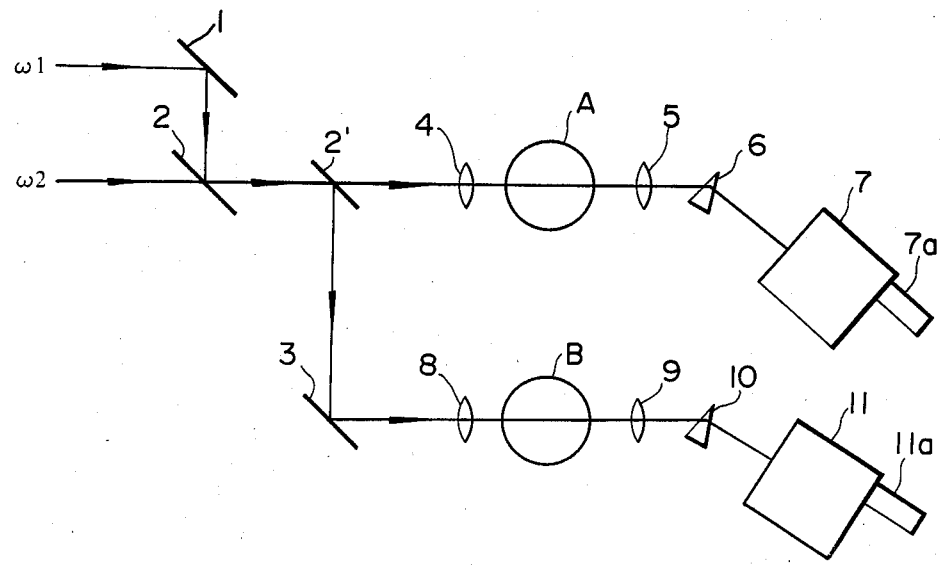
FIG. 3 is a schematic view showing an apparatus for performing quantitative analysis in accordance with conventional CARS.
Figure 4:
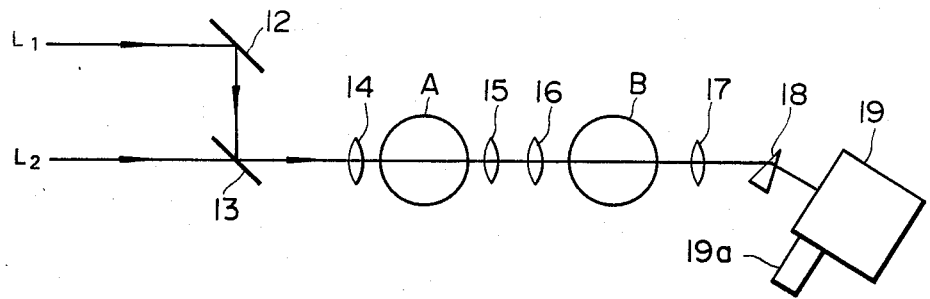
FIG. 4 is a schematic view illustrating an embodiment of the present invention.

FIG. 4 is a schematic view illustrating one embodiment of the invention in which parts having similar functions to those in FIG. 3 are designated by the same reference characters, wherein reference cell A designates a cell for filling with a material to be measured, and B a cell for filling with a reference material. In this embodiment, YAG laser light (wavelength: 532 nm) $L_1$ is utilized for excitation, whilst dye laser light $L_2$ of a wide band is used as another laser light which is applied to the measurement system together with the laser light $L_1$ for excitation. The YAG laser light $L_1$ is reflected by a mirror 12 to be propagated to a dichroic mirror 13, whilst the dye laser light $L_2$ is applied to the dichroic mirror 13 along the direction perpendicular to that of the once-reflected YAG laser light $L_1$. The dichroic mirror 13 reflects the YAG laser light $L_1$, and at the same time, transmits the dye laser light $L_2$. Synthesis of the YAG laser light $L_1$ and the dye laser light $L_2$ is effected by means of the dichroic mirror 13. The synthesized light is applied to a spectrograph 19 through a lens 14, the cell A, a lens 15, a lens 16, the cell B, a lens 17, and a prism 18 for detection by a detector 19a. In this case, a so-called multi-channel detector with different channels which simultaneously detect the respective wavelengths of light received by the spectrograph 19 is employed. The lenses 14–17 focus or refocus the laser light, so that if the focusing ability of the laser light is maintained in this system, such lenses are not necessary.

Figure 5:
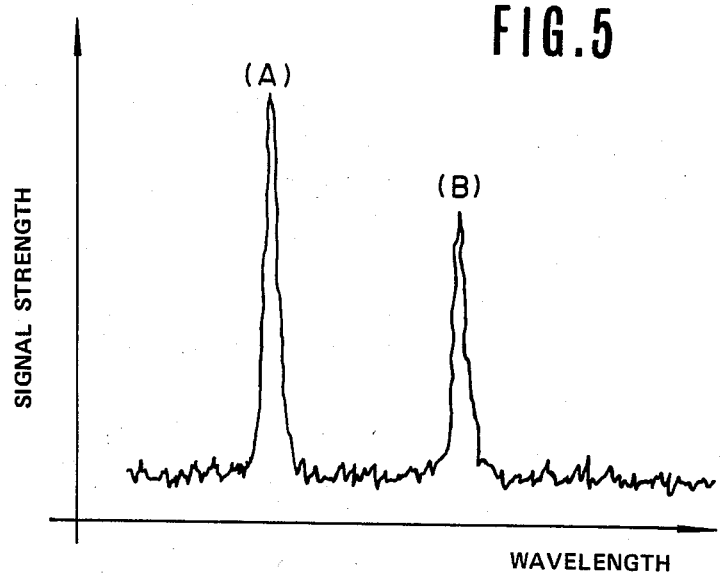
FIG. 5 is a graphical representation indicating an example of intensity determination carried out according to the present invention.

FIG. 5 is a graphical representation showing an example of an intensity measurement made by means of the apparatus shown in FIG. 4, wherein wavelength is plotted as the abscissa and signal strength as the ordinate. In this example, silane $SiH_4$ (Raman wavenumber: 2190 cm$^{-1}$) and carbon monoxide CO (Raman wavenumber: 2143 cm$^{-1}$) are used as a material to be measured and a reference material, respectively. In the graph of FIG. 5, peak (A), which indicates silane $SiH_4$ appears at a wavelength of 476.5 nm, whilst peak (B), which indicates carbon monoxide CO, appears at a wavelength 477.6 nm. The concentration of a material to be measured (silane $SiH_4$ in this case) can be determined from a ratio of strength between these peaks (A) and (B). Furthermore, calibration of absolute concentration is effected in such a manner that a material to be measured is utilized for which the concentration has already been measured in accordance with another method, then a ratio between the concentrations of the material to be measured and the reference material is measured, and the resulting ratio is utilized as the standard.

In the above example of measurement, silane $SiH_4$ and carbon monoxide CO are used as the material to be measured and the reference material, respectively, and anti-Stokes' light generating in vibrational level in respect of these materials is utilized.

Next, a method for measuring a concentration of hydrogen in which anti-Stokes' light generating in rotational levels is utilized will be described hereinbelow.

The apparatus having the construction as shown in FIG. 4 is adopted as an apparatus for measuring the concentration of hydrogen by utilizing anti-Stokes' light emitted between rotational levels, and the measurement is made in such a way that the cell A is filled with a material containing hydrogen to be measured, whilst the cell B is filled with a reference material having a vibrational level corresponding to the rotational level of hydrogen, and a dye laser light $L_2$ of a wide band including the wavelength of the Stokes' light emitted between rotational levels of hydrogen is utilized as another laser light. In this case, $C_2H_6$ (ethane) or $C_6H_6$ (benzene) may be employed as the reference material to fill the aforesaid cell B. The Raman wavenumbers of the ethane and benzene gases are indicated in Table 1 in connection with Raman wavenumber of hydrogen.

TABLE 1

| | | |
|---|---|---|
| $H_2$ (Hydrogen) | Vibrational Level | 4169 cm$^{-1}$ |
| | Rotational Level | 1034 cm$^{-1}$ |
| $C_2H_6$ (Ethane) | | 993 cm$^{-1}$ |
| $C_6H_6$ (Benzene) | | 991 cm$^{-1}$ |

As is apparent from Table 1, when the Raman wavenumber of ethane or benzene is compared with that of hydrogen in the vibrational level, they are significantly different from each other. However, if the Raman wavenumber of either ethane and benzene is compared with that of hydrogen for the rotational level, each difference is within a prescribed range (80 cm$^{-1}$).

In accordance with such construction as mentioned above, the first peak based on the rotational level of hydrogen H$_2$ and the second peak based on the reference material are obtained so that the concentration of hydrogen can be measured from the ratio of strength between the first and second peaks.

Figure 6:
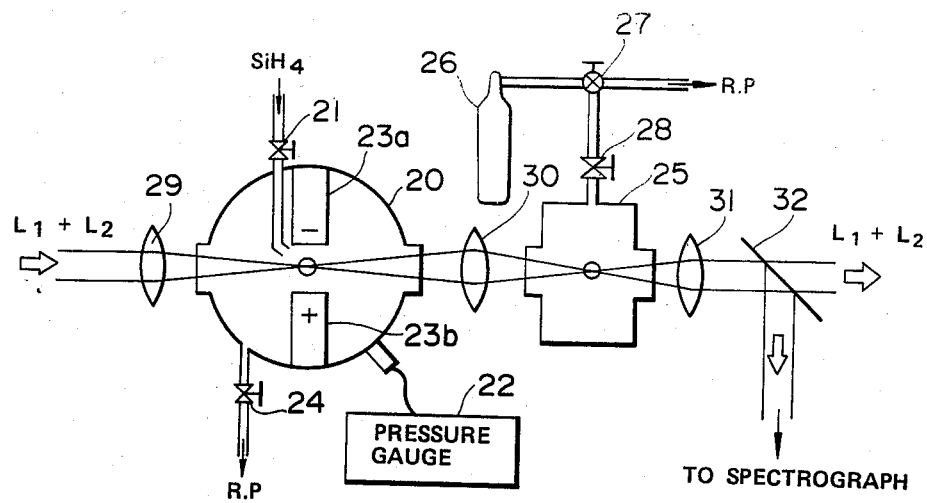
FIG. 6 is a schematic view illustrating another embodiment of the present invention.

FIG. 6 is a schematic view illustrating another embodiment where the present invention is applied to an apparatus for measuring change in concentration of hydrogen by means of plasma discharge in silane SiH$_4$ gas, in which a plasma chamber 20 is filled with silane SiH$_4$ gas through a valve 21. The absolute pressure of the silane SiH$_4$ at this time is measured by a pressure gauge 22. Electrodes 23a and 23b are used for plasma discharge, and a valve 24 is used for exhausting the gas in the plasma chamber 20. Furthermore, a reference cell 25 is filled with ethane or benzene gas, which is used as the reference material and is supplied from a bomb 26 through valves 27 and 28.

In this situation, laser light (synthesized light of YAG laser light L$_1$ and dye laser light L$_2$) L$_1$+L$_2$ is focused with a lens 29 into the plasma chamber 20, then, the light passed through the plasma chamber 20 is refocused with a lens 30 to the reference cell 25. The component relating to anti-Stokes' light in the light which passes through the reference cell 25 and is focused with a lens 31, is separated by means of a dichroic mirror 32 from the laser light L$_1$+L$_2$ so that the separated component is introduced to a spectrograph (not shown). In the spectrograph, when the intensity of the light received is measured by means of a multi-channel detector in every wavelength, a graphical representation as shown in FIG. 5 is obtained. A ratio between the respective peaks for the material to be measured (H$_2$) and the reference material (C$_2$H$_6$ or C$_6$H$_6$) in this case becomes a standard for the following measurement of the concentration of hydrogen.

Thereafter, discharge is effected between the electrodes 23a and 23b in the plasma chamber 20, and a ratio between respective peaks of the material to be measured (H$_2$) and the reference material (C$_2$H$_6$ or C$_6$H$_6$) is measured. Meanwhile, the hydrogen concentration in the plasma chamber varies in accordance with the electric discharge, but the concentration of C$_2$H$_6$ or C$_6$H$_6$ in the reference cell remains unchanged. As a result, change in concentration of hydrogen can be measured from the above-described ratio of peaks.

Although such a case where the present invention is applied to the measurement of change in concentration of hydrogen during plasma discharge in silane gas is described in the above embodiment, it is to be understood that the above case is a mere example and the present invention is applicable to various quantitative analyses. For instance, the present invention may be applied for determining a concentration of silane gas during plasma discharge, the invention is also effective for quantitative analysis of various substances in the combustion process in an engine.

Furthermore, in the embodiments illustrated in FIGS. 4 and 6, the reference material system (the cell B or the reference cell 25) has been disposed after the system of the material to be measured (the cell A or the plasma chamber 20) with respect to the laser light inputted, but this order may be reversed. More specifically, an apparatus may be constructed such that input laser light first passes through the reference material system, and then is inputted to the system of the material to be measured.

Furthermore, any material whose Raman frequency is close to that of ethane or benzene (which is sufficient to enable covering by means of another laser light beam to be applied together with excitation laser light) may be utilized as the reference material of this invention.

What is claimed is:

1. A method of performing quantitative analysis using coherent anti-Stokes Raman spectroscopy (CARS) comprising the steps of:
    (a) filling a first transparent cell with a first material of unknown concentration and having a first Stokes frequency;
    (b) filling a second transparent cell with a second material of known concentration and having a second Stokes frequency;
    (c) separately transmitting laser light of a first frequency; and of a predetermined frequency bandwidth such that said first and second Stokes frequencies lie within said predetermined bandwidth;
    (d) combining said laser light of said first frequency and said pre-determined frequency bandwidth into a single laser beam and transmitting said laser beam through said first and second transparent cells in series;
    (e) directing the anti-Stokes light emitted by said first material in said first transparent cell through said second transparent cell;
    (f) directing the anti-Stokes light emitted by said first material and directed through said second transparent cell and the anti-Stokes light emitted by said second material in said second transparent cell onto a light intensity detector;
    (g) detecting the intensity of anti-Stokes light produced upon passage of said laser light beam through said transparent cells at every wavelength of a spectrum; and
    (h) calculating the concentration of said first material from the ratio of the intensity of the anti-Stokes light corresponding to said second material.

2. A method of performing quantitative analysis using CARS as defined in claim 1, wherein said first material is taken from the group consisting of silane and disilane gas and said second material is carbon monoxide.

3. A method of performing a quantitative analysis using CARS as defined in claim 1, wherein said first material is hydrogen gas and light of said first Stokes frequency is emitted between rotational energy levels of the hydrogen molecule.

4. A method of performing quantitative analysis using CARS as defined in claim 3, wherein said second material is taken from the group consisting of ethane and benzene.

5. An apparatus for performing quantitative analysis using CARS comprising:
    (a) a first laser means for generating laser light of a first frequency;
    (b) a second laser means for generating laser light of a predetermined frequency bandwidth;
    (c) optical means for forming a simple laser beam from said laser light of a first frequency and said laser light of a predetermined frequency bandwidth;
    (d) a first transparent cell filled with a first material of unknown concentration and having a first Stokes frequency lying within said predetermined bandwidth;

(e) a second transparent cell filled with a second material of known concentration and having a second Stokes frequency lying within said predetermined bandwidth, said second transparent cell being disposed in series with said first first transparent cell along the optical path of said single laser beam;

(f) a spectrograph for recording the spectrum of said single laser beam following passage through said first and second transparent cells; and (g) a multi-channel detector for detecting the intensity of anti-Stokes light produced upon passage of said laser beam through said transparent cells at every wavelength of a spectrum, wherein the concentration of said first material can be calculated from the ratio of the intensity of the anti-Stokes light corresponding to said first material to the intensity of the anti-Stokes light corresponding to said second material.

* * * * *